United States Patent [19]

Fiddian-Green

[11] Patent Number: 4,643,192
[45] Date of Patent: Feb. 17, 1987

[54] HOLLOW VISCUS TONOMETRY

[75] Inventor: Richard G. Fiddian-Green, Ann Arbor, Mich.

[73] Assignee: Regents of the University of Michigan, Ann Arbor, Mich.

[21] Appl. No.: 833,287

[22] Filed: Feb. 27, 1986

Related U.S. Application Data

[63] Continuation of Ser. No. 360,718, Mar. 22, 1982, abandoned.

[51] Int. Cl.⁴ .............................................. A61B 5/02
[52] U.S. Cl. ................................. 128/632; 128/749; 128/691
[58] Field of Search ............... 128/749, 780, 632, 635, 128/691

[56] References Cited

U.S. PATENT DOCUMENTS

| | | | |
|---|---|---|---|
| 3,395,710 | 8/1968 | Stratton et al. | 128/749 |
| 3,437,088 | 4/1969 | Bielinski | 128/780 |
| 3,658,053 | 4/1972 | Fergusson et al. | 128/632 |
| 3,983,879 | 10/1976 | Todd | 604/96 |
| 4,221,567 | 9/1980 | Clark et al. | 128/635 |
| 4,244,377 | 1/1981 | Grant | 128/746 |
| 4,259,960 | 4/1981 | Taylor | 604/96 |
| 4,265,249 | 5/1981 | Schindler | 128/635 |
| 4,304,239 | 12/1981 | Perlin | 128/786 |

Primary Examiner—Lee S. Cohen
Assistant Examiner—John C. Hanley
Attorney, Agent, or Firm—Harness, Dickey & Pierce

[57] ABSTRACT

Ischemia in a hollow internal organ can be detected in its incipient stages by obtaining a $CO_2$ sample from within the organ of interest, measuring the partial pressure of $CO_2$ sample, measuring the bicarbonate concentration of an arterial blood sample, and on the basis of these two measurements calculating the pH of the wall of the organ. The value of the pH is an indicator of the onset of ischemia in the organ. The $CO_2$ sample is obtained by a novel catheter, multiple embodiments of which are disclosed.

5 Claims, 4 Drawing Figures

HOLLOW VISCUS TONOMETRY

This is a continuation of application Ser. No. 360,718 filed Mar. 22, 1982, now abandoned.

BACKGROUND AND SUMMARY OF THE INVENTION

This invention relates to medical diagnostic equipment and methods and is particularly concerned with hollow viscus tonometry.

Stress ulceration and intestinal ischemia are two serious problem that plague physicians involved in the management of patients in intensive care units. Intestinal ischemia, in particular, has an insidious onset and may not be detected until days after the intestine has become gangrenous. A delay in the diagnosis of intestinal ischemia may have devastating consequences for a patient. The availability of means for early diagnosis and management of patients with these problems would have immediate applicability in all intensive care units, especially where the procedure can be conveniently conducted with reasonable safety and reliability.

It has been established that a fall in the intramuscosal pH may precede the development of stress ulceration. One aspect of the invention involves the discovery, in the laboratory, that a fall in intrasmucosal pH also occurs within minutes of inducing intestinal ischemia in dogs. The fall in pH in intestinal mucosa, and hence the liklihood of stress ulceration or ischemia, can be reliably calculated from a $pCO_2$ (partial pressure of $CO_2$) in luminal fluid and the bicarbonate concentration in arterial blood. The method of calculating the pH in intestinal mucosal tissue, pursuant to principles of the invention, has been validated by direct measurements under a variety of conditions simulating clinical problems. A correlation coefficient in the order of 0.92 to 0.95 has been obtained in each of sixteen dogs. It will be readily recognized that the validity of the procedure is inherently extensible to humans.

To measure the $pCO_2$ in the lumen of the gut it is necessary to obtain a sample of fluid that has been in contact with the wall of the gut for a certain time period, usually at least half an hour. It is difficult to aspirate fluid from the lumen of the gut with any consistency, for any fluid instilled into the lumen passes into distal and proximal regions. It is much easier to obtain samples from the stomach, but samples obtained from the stomach frequently contain foreign material that can damage a gas analyzer.

A particular aspect of the invention involves the creation of a new and unique catheter via which the desired sample or samples can be obtained without the complications of prior techniques. One embodiment of the new and unique catheter comprises a catheter tube having a walled sampling chamber on the tube with the sampling chamber being in communication with the hollow interior of the tube. The wall of the sampling chamber comprises a material which is substantially impermeable to liquid yet is highly permeable to gas. One suitable material is polydimethylsiloxane elastomer.

In use the catheter is introduced into a patient to place the sampling chamber at a desired site within the organ of interest. An aspirating liquid fills the interior of the sampling chamber. The sampling chamber is left in place at the desired sampling site long enough to allow the gases present to diffuse through the wall of the sampling chamber into the aspirating liquid. The time should be long enough for the gases to equilibrate. The liquid impermeable nature of the sampling chamber wall material prevents both the aspirating liquid from leaking out of the chamber and also the intrusion of any liquids into the aspirating liquid. After the appropriate amount of placement time has elapsed the aspirating liquid is aspirated along with the gases which have diffused into it. The sample thus obtained is analyzed for gas content, in particular for $pCO_2$. In this way the $pCO_2$ within the lumen of the gut can be reliably measured with the fluid being free from lumenal debris.

In carrying out the diagnostic method of the invention the $pCO_2$ measurement is utilized in conjunction with a measurement of the bicarbonate concentration in an arterial blood sample of the patient for determining the pH of the tract wall.

Depending upon the particular condition of a given patient, the catheter may be left in place and samples may be taken at periodic intervals so that pH values may be periodically calculated. The procedure has a high reliability in accurately diagnosing intestinal ischemia in its incipient stages and such detection can be useful in treating the patient so that the potentially devestating consequences resulting from less timely detection may often be avoided.

The invention has applicability to many hollow internal organs although in the techniques described in detail herein the invention involves diagnosis within the gastrointestinal tract system. Depending upon the particular site or sites of interest within a patient, different types of catheters embodying principles of the invention may be appropriately used. One embodiment involves a catheter as described above. In that embodiment the catheter has a single sampling chamber and a single walled tube. Another embodiment contemplates the use of multiple individual single sampling chamber catheters of varying lengths bundled together to form a multiple sampling site catheter. Still another embodiment involves the use of a sump-type nasogastric tube. Yet another embodiment comprises a pliable catheter with a mercury bag at its end which may be used for certain procedures.

In use of an embodiment that employs multiple sampling chambers, the pH in intestinal mucosal tissue at one site may be calculated and compared with the calculated pH values at other sites. This analysis can be a useful diagnostic aid to the attending physician. In the case of an abdominal aortic resection a multiple sampling chamber type catheter may be placed intraluminally in series in the colon at the time of the resection, and it may be used to aid in the early detection of colonic ischemia that occurs insidiously in approximately five percent of the patients subjected to this major operation. A multiple sampling chamber embodiment may also be introduced into the small intestine to monitor the pH and hence perfusion of the gut in patients with low flow states. In critically ill patients who require a nasogastric tube, a single sampling chamber embodiment may be incorporated into a conventional nasogastric tube and placed in the patient's stomach.

It is further contemplated that the invention may be practiced in connection with diagnosis of the billary tract, urinary tract and pancreas for monitoring pH and hence perfusion of the associated organs.

In connection with this invention, a preliminary novelty search developed the following U.S. Pat. Nos. 2,470,665; 3,227,154; 3,548,805; 3,572,315; 3,952,730;

and 4,168,703, none of which are deemed pertinent to the claims of the present invention.

The foregoing features and benefits of the invention in its several aspects, along with additional features and benefits, will be seen in the ensuing description and claims which should be considered in conjunction with the accompanying drawings. The drawings disclose presently preferred embodiments of catheters which embody principles of the invention and are used in the diagnostic aspects of the invention.

Fig, 4 is still another embodiment of catheter embodying principles of the invention.

DESCRIPTION OF THE PREFERRED EMBODIMENT

Figure 1:
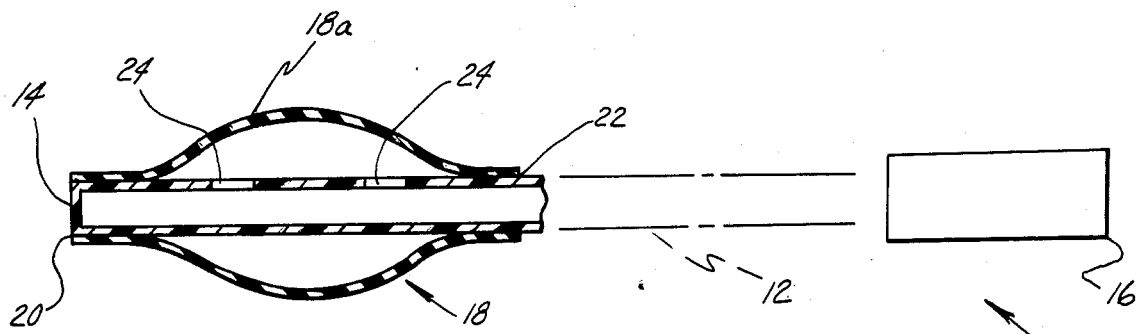
FIG. 1 is a diagramatic view of a catheter embodying principles of the invention.

FIG. 1 illustrates a first embodiment of catheter 10. The catheter comprises a length of suitable tubing 12 one end 14 of which is closed, and the opposite end of which contains a connector such as a luer-lock 16 or equivalent. A sampling chamber 18 is provided on the tube adjacent the closed end 14.

The illustrated embodiment utilizes a tubular element 18a forming the sampling chamber wall. The preferred form of tubular element is polydemethylsiloxane elastomer. The tubular element has an internal diameter which allows it to be fitted over the tubing 12. The axial end segments of the tubular element 18a are secured to the outer wall of tube 12 at the locations indicated by the reference numerals 20 and 22. The attachment may be made in any suitable fashion with adhesive being a suitable attachment medium. Thus, the ends of the tubular element 18a are sealed in a closed relationship to the outer wall of the tube 12 thereby forming the sampling chamber 18 adjacent tube end 14. The wall material of the sampling chamber has a certain elasticity so as to allow the enclosure to assume a slightly ballooned or ovoidal shape when filled by aspirating liquid, as will be explained hereinafter.

Before the tubular element 18a is inserted over tube 12, suitable apertures 24 (shown on an enlarged scale in the drawing) are provided in the wall of tube 12 so that after assembly of the tubular element 18a the tube 12 the apertures 24 provide communication between the interior of tube 12 and the interior of the sampling chamber 18.

The material of the tubular element 18a possesses a characteristic whereby it is poorly permeable to liquid fluid while it is freely permeable to gaseous fluid. This property is important in practice of the invention. The material is also substantially impervious to the contents of the intestinal tract.

In one form of use the catheter is introduced into a patient by being fed into the colon from the anus and positioned intraoperatively. A suitable aspirating fluid, such as a saline solution, is introduced via the luer lock 16, tube 12, and apertures 24 to fill the interior of the sampling chamber. The fluid passes through the apertures 24 filling the interior of the sampling chamber such that the sampling chamber assumes a balloon-like state.

According to the method of the invention the catheter is placed such that the sampling chamber is at a desired sampling site in the internal organ of interest. It is left at this site for a sufficient amount of time to allow gases, carbon dioxide being the particular gas of interest, to diffuse across the wall of the chamber into the aspirating liquid. Desirably the length of time should be sufficient to allow the gases to equilibrate. For example, one half hour may be suitable in certain applications.

The aspirating liquid containing the carbon dioxide gas is then withdrawn via the luer end lock 16. The aspirated sample thus obtained is subjected to analysis by a conventional gas analyzer to measure the $pCO_2$ content of the lumenal fluid. A measurement of the bicarbonate concentration in the arterial blood of the patient is also obtained. These two measurements are then used to calculate the pH of the tract. Measurements may be taken at periodic intervals in the same manner and in this way a record of pH values can be established.

The invention, in one respect, involves recognition of the principle that the partial pressure of gas in the lumen of the gastrointestinal tract is the same or very close to that in the wall of the gastrointestinal tract under a steady state condition and hence, can be used as a measure of the partial pressure of gas, especially $CO_2$, in the wall of that part of the gastrointestinal tract. The pH in the wall of the gastrointestinal tract can be calculated from this value if the bicarbonate concentration in arterial blood is also known. With the catheter of the invention the partial pressure of gas within the gastrointestinal tract can be readily measured because it allows a clear fluid sample, free of objectionable particulates and the like, to be obtained.

As explained earlier, a drop in the intramucosal pH has been found to accompany development of intestinal ischemia, and therefore the pH monitoring can be used to monitor for the incipiency of this potentially devestating condition. The earlier warning obtained with the invention offers the possibility of earlier treatment to counteract the condition.

Figure 2:
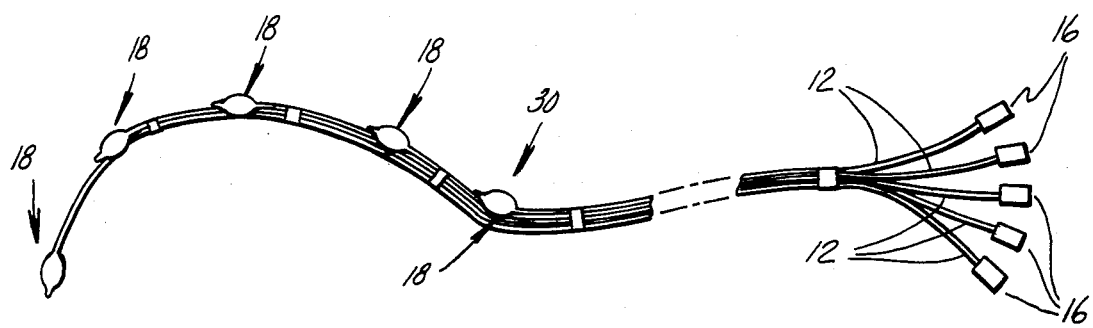
FIG. 2 is another embodiment of catheter embodying principles of the invention.

FIG. 2 illustrates a further embodiment of the catheter 30. This embodiment is also useful in the colon. The catheter 30 comprises multiple sampling chambers 18 at spaced locations along the length of the catheter. In this regard the catheter 30 is constructed as a bundle of individual catheters, such as the catheter 10 of FIG. 1, the individual catheters having various lengths. The illustrated example has five sampling chambers. This allows measurements to be taken at five different sites within the organ of interest and is useful for monitoring pH values not only in time at a particular sampling site but also in respect to concurrent pH measurements at different sites.

Figure 3:
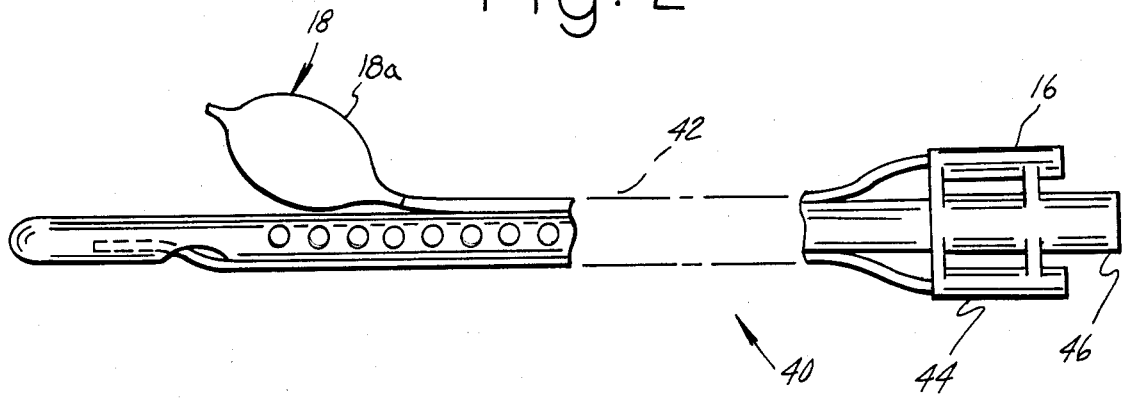
FIG. 3 is yet another embodiment of catheter embodying principles of the invention.

FIG. 3 illustrates a further embodiment of catheter 40 which comprises a tube 18a forming the wall of the sampling chamber; however the tube 42 comprises a conventional double lumen nasogastric sump tube with a third lumen for the sampling chamber 18. The air and aspiration ports 44, 46 are of the nasogastric tube and the luer-end lock 16 is for the third lumen which leads to the sampling chamber 18. The catheter 40 is intended for use in the stomach. In this regard the catheter may be inserted into a patient in the same manner as a nasogastric tube, and the aspirating fluid for obtaining the $CO_2$ measurement is introduced and aspirated via luer lock 16 in the same manner as that for the previously described catheters.

Figure 4:
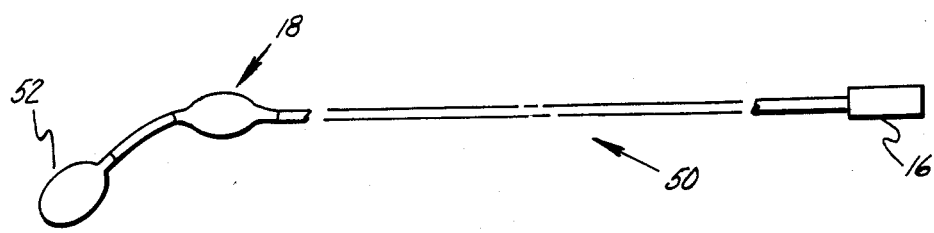

FIG. 4 illustrates a still further embodiment of catheter 50 which is the same as the embodiment 10 of FIG. 1 except that the end 14 includes a sealed mercury bag 52. This catheter is intended for use in the small intestine, and it should be very soft and pliable with the mercury bag allowing peristalsis to position the tube in the small intestine. It should be long enough to reach the terminal ileum, and the same length as a colonscope would be more than adequate.

If desired, any of the embodiments of single catheter may be bundled together as in the manner of FIG. 2 so as to provide multiple sampling sites in any catheter construction.

Desirably the volume of the sampling chamber should be relatively small in order to facilitate rapid equilibration of gas yet it must be large enough so that a suitable sample of about one milliliter for use in the gas analyzer can be withdrawn via the element 16. For example, around two milliliters is a suitable volume. The tubes such as the tube 12 should be of small caliber to insure as small a dead space as possible within the patient when in use. Tube 12 should also have as small a fluid volume (say about two-tenths milliliter) so that a minimum of aspirating liquid need be withdrawn at element 16 in advance of the sample from the chamber 18. The tubewall 12 should also be impermeable to gas. The luer end locks are conventional for connection to a syringe when aspirating fluid is to be introduced or withdrawn. The catheters may also contain rapid opaque markers for use in verifying position of the sampling chambers in the gut.

Where the catheter is to be left in the lumen of the gut for an extended period of time, for example several days, it should be soft enough to be allowed to remain in this position without damage to the wall of the gut. To facilitate insertion, for example into the colon, the catheter should be firm enough to allow for proper feeding. In this regard it may be appropriate to use a wire stent during insertion to facilitate positioning of the catheter with the wire stent being removed after proper positioning has been obtained.

While the preferred embodiment has been disclosed in connection with monitoring of the gastrointestinal tract it will be appreciated that its principles are applicable to other hollow internal organs to monitor pH and hence perfusion of those organs. Also while a preferred detailed construction for a catheter, such as described in FIG. 1, has been disclosed, it will be appreciated that other constructions may be developed which are equally as suitable. The disclosed construction however is presently preferred for the reason that it is readily fabricated using existing available materials. Other embodiments may include other, but equivalent materials for the sampling chamber wall. They may also differ in the specific fabrication details. As an example, the sampling chamber may be eccentric rather than symmetric about the tube 12.

While a preferred embodiment of the invention has been disclosed, it will be appreciated that principles of the invention, as set forth in the following claims, are applicable to other embodiments.

What is claimed is:

1. A method for detecting the onset of ischemia in a hollow internal organ which comprises providing a catheter having a catheter tube; and a walled sampling chamber on the tube in communication with the interior of the tube; the wall of said walled sampling chamber comprising a material which is freely permeable to carbon dioxide gas in solution but poorly permeable to liquid fluid, introducing the catheter into the organ of interest so that the sampling chamber is disposed at a desired sampling site and leaving the sampling chamber disposed at the sampling site for a length of time sufficient to allow any carbon dioxide gas present at the sampling site to diffuse across the wall of the sampling chamber into aspirating liquid contained within the sampling chamber, withdrawing at least a portion of said aspirating liquid containing any diffused carbon dioxide gas via the catheter tube, analyzing the sample thus withdrawn for carbon dioxide, directly measuring the bicarbonate concentration of the article blood of the patient, determining of pH of said hollow internal organ at the sampling site on the carbon dioxide and bicarbonate measurements thus obtained, and determining whether ischemia is present on the basis of of pH determination.

2. A method according to claim 1 wherein the hollow internal organ is the gut.

3. A method according to claim 2 wherein the portion of the gut of interest is the colon.

4. A method according to claim 2 wherein the portion of the gut of interest is the small intestine.

5. A method according to claim 2 wherein the portion of the gut of interest is the stomach.

* * * * *

UNITED STATES PATENT AND TRADEMARK OFFICE
CERTIFICATE OF CORRECTION

PATENT NO. : 4,643,192

DATED : 02/17/87

INVENTOR(S) : Richard G. Fiddian-Green

It is certified that error appears in the above-identified patent and that said Letters Patent is hereby corrected as shown below:

| | |
|---|---|
| References cited: | "Grant" should be --Grams--; |
| Column 1 Line 30 | "liklihood" should be --likelihood--; |
| Column 3 Line 19 | "Fig," should be --FIG.--; |
| Column 3 Line 27 | "luer lock 16" should be --luer-end lock 16--; |
| Column 3 Line 50 | "and" should be inserted between --12 & the--; |
| Column 3 Line 63 | "luer lock 16" should be --luer-end lock 16--; |
| Column 4 Line 11 | "luer end" should be --luer-end--; |
| Column 4 Line 67 | "luer lock 16" should be --luer-end lock 16--; |
| Column 5 Line 27 | "luer end" should be --luer-end--; |
| Column 6 Line 34 | "article" should be --arterial--; |
| Column 6 Line 38 | "of of" should be --of--. |

Signed and Sealed this

Twenty-ninth Day of September, 1987

Attest:

DONALD J. QUIGG

*Attesting Officer*   *Commissioner of Patents and Trademarks*